(12) United States Patent
Mitts

(10) Patent No.: US 12,042,420 B2
(45) Date of Patent: Jul. 23, 2024

(54) URINE COLLECTION BAG ASSEMBLY

(71) Applicant: Cheryl A. Mitts, Las Vegas, NV (US)

(72) Inventor: Cheryl A. Mitts, Las Vegas, NV (US)

( * ) Notice: Subject to any disclaimer, the term of this patent is extended or adjusted under 35 U.S.C. 154(b) by 0 days.

(21) Appl. No.: 18/394,394

(22) Filed: Dec. 22, 2023

(65) Prior Publication Data

US 2024/0130887 A1 Apr. 25, 2024

Related U.S. Application Data

(63) Continuation-in-part of application No. 17/239,476, filed on Apr. 23, 2021, now abandoned, which is a continuation of application No. 15/858,395, filed on Dec. 29, 2017, now abandoned, which is a continuation of application No. 15/429,048, filed on Feb. 9, 2017, now Pat. No. 9,867,731.

(60) Provisional application No. 62/331,794, filed on May 4, 2016.

(51) Int. Cl.
*A61F 5/44* (2006.01)
*A61B 50/22* (2016.01)
*A61M 25/00* (2006.01)
*A61M 39/02* (2006.01)

(52) U.S. Cl.
CPC ........... *A61F 5/4405* (2013.01); *A61B 50/22* (2016.02); *A61F 5/44* (2013.01); *A61F 5/4404* (2013.01); *A61F 5/4407* (2013.01); *A61M 25/0017* (2013.01); *A61M 2039/0202* (2013.01)

(58) Field of Classification Search
CPC ........ A61F 5/44; A61F 5/4405; A61F 5/4407; A61M 2039/0202; A61M 25/0017; A61B 50/22
See application file for complete search history.

(56) References Cited

U.S. PATENT DOCUMENTS

| | | |
|---|---|---|
| 3,780,736 A | 12/1973 | Chen |
| 3,965,910 A | 6/1976 | Fischer |
| 4,000,649 A | 1/1977 | Hanifl |
| 4,306,705 A | 12/1981 | Svensson |
| 4,340,148 A | 7/1982 | Beckham |
| 4,512,770 A | 4/1985 | Cianci et al. |
| 4,521,213 A | 6/1985 | Steigerwald |
| 4,723,950 A | 2/1988 | Lee |
| 4,725,268 A | 2/1988 | Ostensen et al. |
| 4,904,245 A | 2/1990 | Chen et al. |
| 4,913,161 A | 4/1990 | Villari et al. |
| 4,936,837 A * | 6/1990 | Wexler ................ A61F 5/4407 604/326 |

(Continued)

FOREIGN PATENT DOCUMENTS

| | | |
|---|---|---|
| JP | 2001061876 | 3/2001 |
| JP | 2005052375 | 3/2005 |
| WO | 9101120 | 2/1991 |

*Primary Examiner* — Benjamin J Klein
(74) *Attorney, Agent, or Firm* — Cislo & Thomas, LLP

(57) ABSTRACT

An improved urine collection bag assembly is presented. The improved urine collection bag assembly of the present invention features a one-way flow control valve to prevent the backflow of urine into a urinary catheter and subsequently, into a patient's bladder. The improved urine collection bag also features at a bacterial monitoring wick, an air vent, and a sampling port among other features. In an exemplary embodiment, the one-way flow control valve is a duckbill style valve and the sampling valve is a slider style valve.

20 Claims, 10 Drawing Sheets

(56) References Cited

U.S. PATENT DOCUMENTS

| | | |
|---|---|---|
| 4,976,697 A | 12/1990 | Walder et al. |
| 5,300,049 A | 4/1994 | Hogan |
| 5,312,383 A | 5/1994 | Kubalak |
| 5,616,138 A | 4/1997 | Propp |
| 5,807,345 A | 9/1998 | Grabenkort |
| D399,307 S | 10/1998 | Leigh |
| 5,919,146 A | 7/1999 | Propp |
| D478,662 S | 8/2003 | Flinchbaugh |
| 7,410,481 B1 | 8/2008 | Mitts et al. |
| 7,780,640 B1 | 8/2010 | Amador |
| 7,828,269 B2 | 11/2010 | Iversen |
| 7,850,677 B2 | 12/2010 | Blake et al. |
| 8,684,331 B2 | 4/2014 | Spolski |
| 8,702,681 B2 | 4/2014 | Douglas et al. |
| 9,867,731 B2 | 1/2018 | Mitts |
| 2004/0204699 A1 | 10/2004 | Hanly et al. |
| 2006/0025724 A1 | 2/2006 | Chen |
| 2007/0203464 A1 | 8/2007 | Green et al. |
| 2007/0213639 A1 | 9/2007 | Salvadori |
| 2008/0281284 A1 | 11/2008 | Garfield et al. |
| 2009/0062755 A1 | 3/2009 | Burgess et al. |
| 2011/0054426 A1 | 3/2011 | Stewart |
| 2011/0265825 A1 | 11/2011 | Rogers et al. |
| 2012/0041400 A1 | 2/2012 | Christensen |
| 2012/0116335 A1 | 5/2012 | Tanghoej |
| 2013/0245496 A1* | 9/2013 | Wells ................ A61M 25/0017 600/581 |
| 2013/0274686 A1 | 10/2013 | Ziebol et al. |
| 2014/0039349 A1 | 2/2014 | Moghe et al. |
| 2015/0126975 A1 | 5/2015 | Wuthier |
| 2017/0319373 A1* | 11/2017 | Mitts ........................ A61F 5/44 |
| 2023/0091798 A1* | 3/2023 | Price ................ A61M 25/0017 600/581 |

\* cited by examiner

URINE COLLECTION BAG ASSEMBLY

CROSS-REFERENCE TO RELATED APPLICATION

This application is a continuation-in-part of U.S. patent application Ser. No. 17/239,476 filed on Apr. 23, 2021, which is a continuation of U.S. patent application Ser. No. 15/858,395, filed on Dec. 29, 2017, which is a continuation of U.S. patent application Ser. No. 15/429,048 (now U.S. Pat. No. 9,867,731), filed on Feb. 9, 2017 and issued on Jan. 16, 2018, which claims the benefit of U.S. Provisional Patent Application Ser. No. 62/331,794, filed on May 4, 2016, which are incorporated in their entirety herein by this reference.

BACKGROUND OF THE INVENTION

Field of the Invention

The present invention relates generally to the field of medical devices and more particularly to an improved urine collection bag for the collection and disposal of urine in patients which require urinary tract catheterization, as may be necessary due to a variety of medical conditions.

Background

Normal bladder function includes the cyclic filling of the bladder with urine and periodic voiding when pressure buildup reaches a certain level which may vary within a limited range from patient to patient. The bladder muscles control voiding of the bladder. When healthy, the bladder periodically empties or washes out, allowing bacteria and other potentially harmful micro-organisms to exit the body thus preventing infection.

A variety of medical conditions can interfere with the normal function of the bladder. When patients have difficulty urinating, a Foley catheter or other indwelling catheter is often employed to open the bladder allowing the voiding of urine. In typical applications, the catheter is connected or coupled to a urine collection bag, typically through a length of tubing, and urine from the bladder is allowed to drip into the collection bag. When the bag becomes full, a nurse typically applies a clamp to the tubing ahead of the bag, decouples the bag and replaces it with a new bag. After a new bag is attached, the clamp may be removed.

Many problems may arise with catheters and urine collection bags used as described above and, most particularly, catheter associated urinary tract infections. Urinary tract infections are among the most common type of healthcare related infection. Virtually all healthcare related urinary tract infections are caused by the use of instrumentation in the urinary tract. Catheter related urinary tract infections are associated with increased morbidity, hospital costs and length of stay. Urine collection bags are often reservoirs for drug resistant bacteria and urine backflow from a collection bag is frequently the primary cause of urinary tract infections.

Medical professionals generally believe that the most common cause of urinary tract infections is the backflow of urine into the urinary tract when the urine collection bag is raised above the bladder level. Pathogens may enter the urinary tract by migration from a contaminated collection bag along the internal lumen of the catheter.

Accordingly, there is a need in the art for a urine collection bag that prevents or reduces the possibility of urine backflow into a patient's bladder. Such a bag would dramatically reduce the risk of a urinary tract infection in the patient. Reductions in urinary tract infections would have a positive effect on patient health and would decrease the overall cost of treating patients with urinary tract catheters.

SUMMARY OF THE INVENTION

The urine collection bag assembly of the present invention includes a urine collection bag having an inlet and an outlet, a one-way flow control valve at the inlet and a sampling valve at the outlet. Three embodiments of the urine collection bag assembly are presented. In two embodiments, the one-way flow control valve is mounted at the top of, and just outside of, the urine collection bag and in another embodiment, the one-way flow control valve is mounted on the side of the urine collection bag. In each of the embodiments, the one-way flow control valve includes an inlet opening which connects via a length of flexible tubing to a urinary catheter and an outlet opening that drains into the urine collection bag.

The sampling valve of the improved urine collection bag assembly is located at a lower end of the urine collection bag. The sampling valve allows for urine samples to be drawn from the bag. The sampling valve is a slide style valve which allows urine to flow from the urine collection bag through an inlet to the sampling valve and through an outlet located at a lower end of the sampling valve. The lower end of the sampling valve includes a threaded connection for the ready attachment of accessories such as urine collection or sampling bottles, as well as the attachment of screw caps when the sampling valve is not in use.

The improved urine collection bag assembly improves upon the prior art by providing a one-way flow control valve in the fluid path between the urine collection bag and a urinary catheter. Therefore, in the event the urine collection bag assembly is elevated above the patient's bladder, urine is prevented from back-flowing from the collection bag, through the catheter and into the patient's bladder.

One embodiment of the urine collection bag assembly also features a bacterial monitoring wick, an air vent, a sampling valve clip, a sampling port, among other features. The bacterial monitoring wick is in direct contact with urine drainage flow. If a patient's urine becomes contaminated, suggesting an infection, the bacterial monitoring wick will change color, thereby promoting replacement of the urine collection bag assembly and of the catheter which directs urine into the collection bag. The air vent of the urine collection bag assembly is a pressure release valve which is configured to release air upon air accumulating the in the urine collection bag and exceeding a predetermined pressure. The sampling port which may be a needle sampling port or a needle free sampling port allows urine samples to be drawn with a syringe.

Optionally, the one-way flow control valve of the urine collection bag assembly and a catheter connection tube interconnecting the urine collection bag assembly and a urinary catheter may be equipped with antibacterial coatings to further minimize the likelihood that any urine residue that may reside in the catheter connection tube or the one-way flow control valve could cause a urinary tract infection should that residue inadvertently backflow into a patient's bladder.

The above and other features of the invention will become more apparent from the following detailed description.

DETAILED DESCRIPTION OF THE PREFERRED EMBODIMENTS

The present invention will now be described more fully hereinafter with reference to the accompanying drawings, in which preferred embodiments of the invention are shown. The invention may, however, may be embodied in many different forms and should not be construed as being limited to the embodiments set forth herein. Rather these embodiments are provided so that this disclosure will be thorough and complete, and will fully convey the scope of the invention to those skilled in the art. Like numbers refer to like elements throughout.

The first embodiment 10A of the urine collection bag assembly of the present invention improves upon the prior art and reduces urinary tract infections by providing a one-way flow control valve 18 in the fluid path between a urine collection bag 12 and a urinary catheter (not shown). Therefore, in the event the first embodiment 10A of the urine collection bag assembly is elevated above the level of the patient's bladder, a situation which commonly occurs when urine collection bags are hung from a rack, urine is prevented from back-flowing from the urine collection bag assembly, through the catheter and into the patient's bladder.

Figure 1:
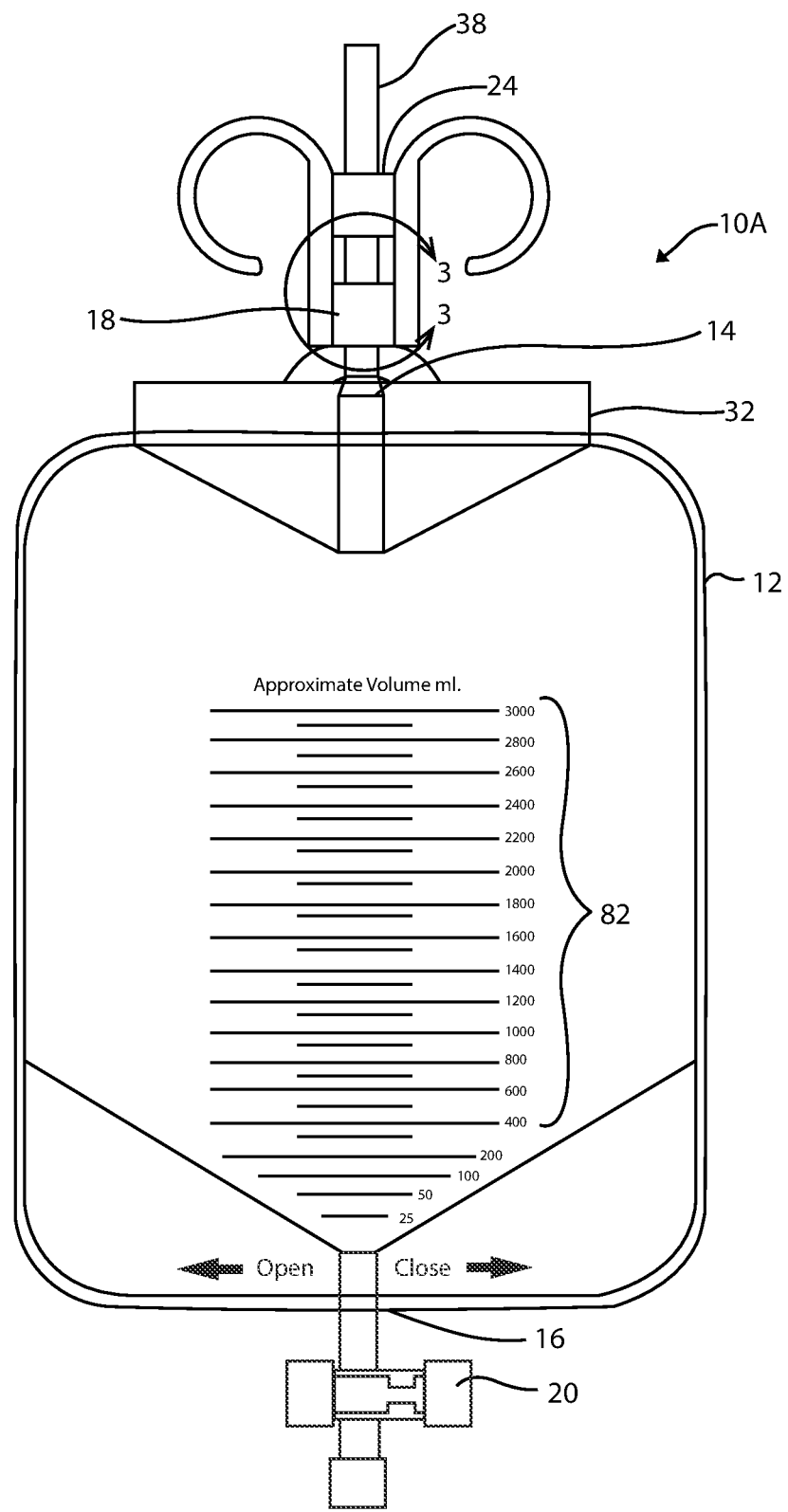
FIG. 1 is a schematic front plan view of a first exemplary embodiment of the urine collection bag of the present invention.
Figure 2:
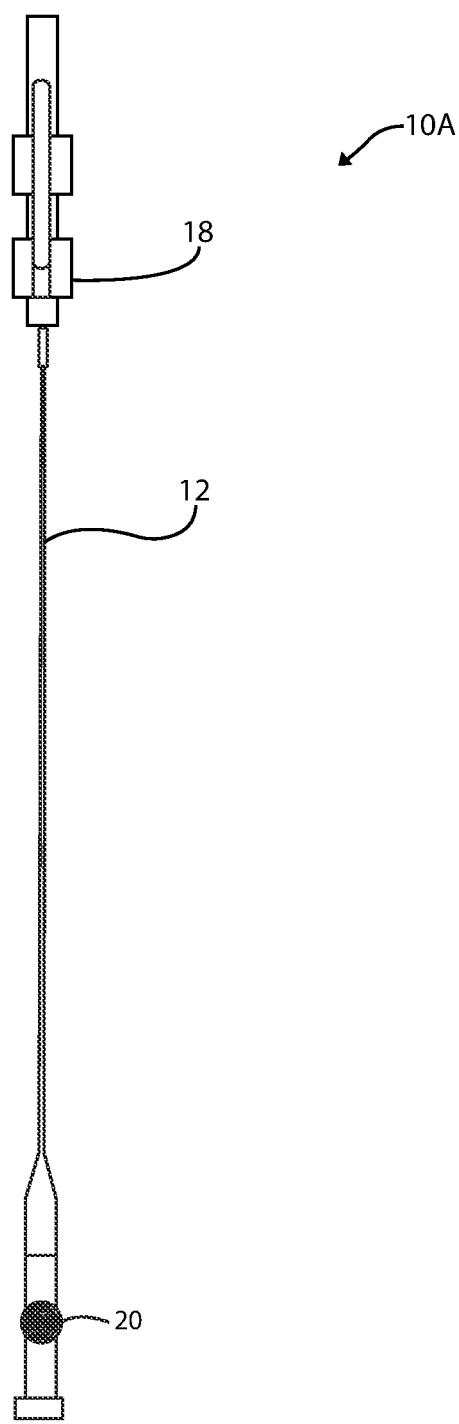
FIG. 2 is a schematic side view of the urine collection bag of FIG. 1.
Figure 3:
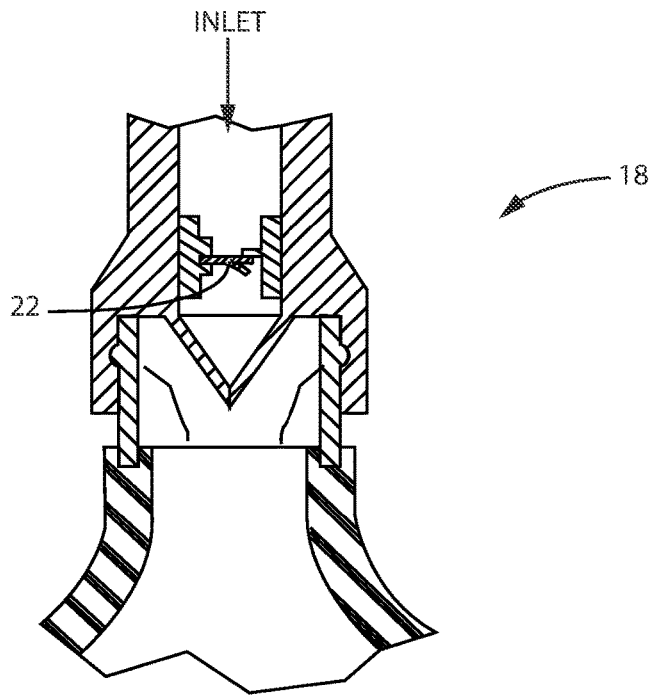
FIG. 3 is a schematic detail view of an exemplary one-way flow control valve suitable for use with the urine collection bag assembly of the present invention.
Figure 4:
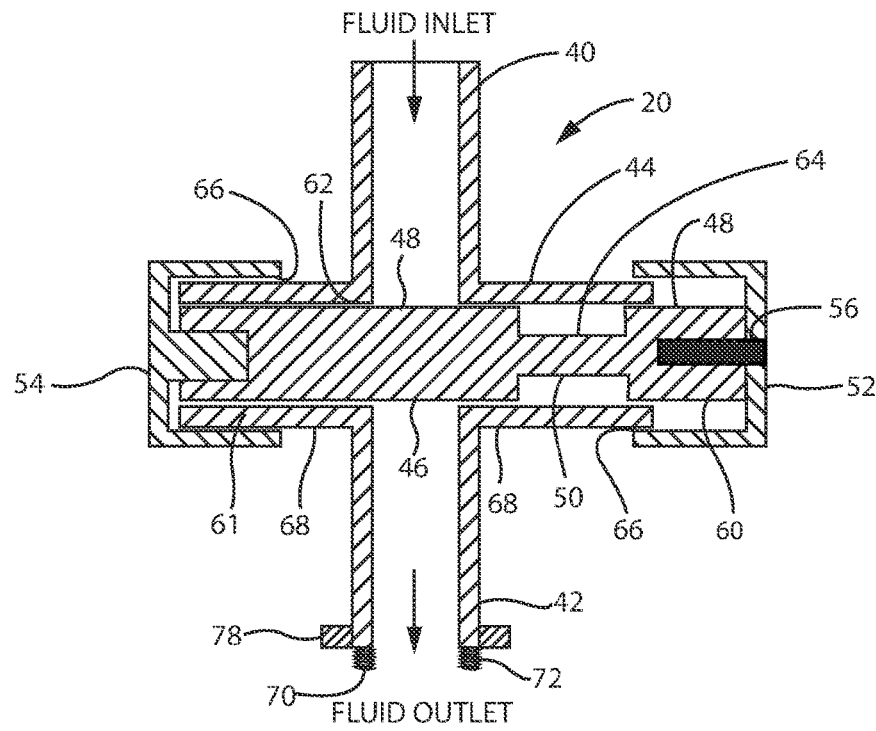
FIG. 4 is a schematic, cross-sectional view of a sampling valve of the present invention.
Figure 5:
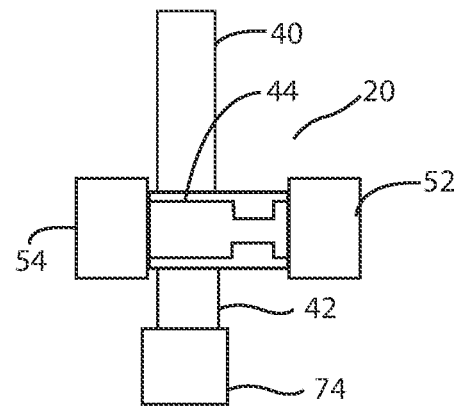
FIG. 5 is a schematic, front view of a sampling valve of the present invention shown in the closed position.
Figure 6:
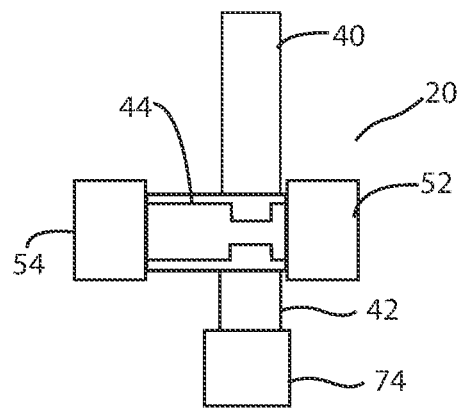
FIG. 6 is a schematic, front view of a sampling valve of the present invention shown in the open position.
Figure 7:
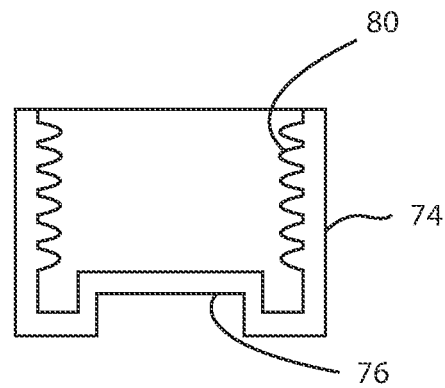
FIG. 7 is a schematic, cross-sectional view of a screw cap suitable for use with the sampling valve assembly of the present invention.

With reference to FIGS. 1-3, the first embodiment 10A of the urine collection bag assembly of the present invention includes the urine collection bag 12 having an inlet 14 and an outlet 16. The first embodiment 10A of the urine collection bag assembly also includes the one-way flow control valve 18 disposed exterior to the urine collection bag 12 and above the inlet 14. At the outlet 16 of the urine collection bag 12 is located a sampling valve 20 exterior to the urine collection bag 12 and below the outlet 16. The one-way flow control valve 18, urine collection bag 12 and sampling valve 20 being in fluid communication.

The one-way flow control valve 18 has an inlet and an outlet, the outlet of the one-way flow control valve 18 being connected to the inlet 14 of the urine collection bag 12. The one-way flow control valve 18 should present little resistance to fluid flow in one direction and high resistance to fluid flow in an opposite direction. Flap style flow control valves are well suited for use in the urine collection bag assembly of the present invention. Flap style valves incorporate a flexible flap element 22 (see FIG. 3) which opens in one direction in the presence of fluid flow, but closes if a reverse flow condition is experienced. One design for a suitable flap style flow control valve is disclosed in U.S. Pat. No. 7,410,481 entitled "URETHRAL CATHETER DEVICE AND METHOD OF USING," which issued to Cheryl Mitts et al. on Aug. 12, 2008. Several other types of one-way fluid flow control valves including needle valves and check ball style valves are known in the valve design art and may also be suitable for use in with the improved urine collection bag assembly of the present invention.

Figure 8:
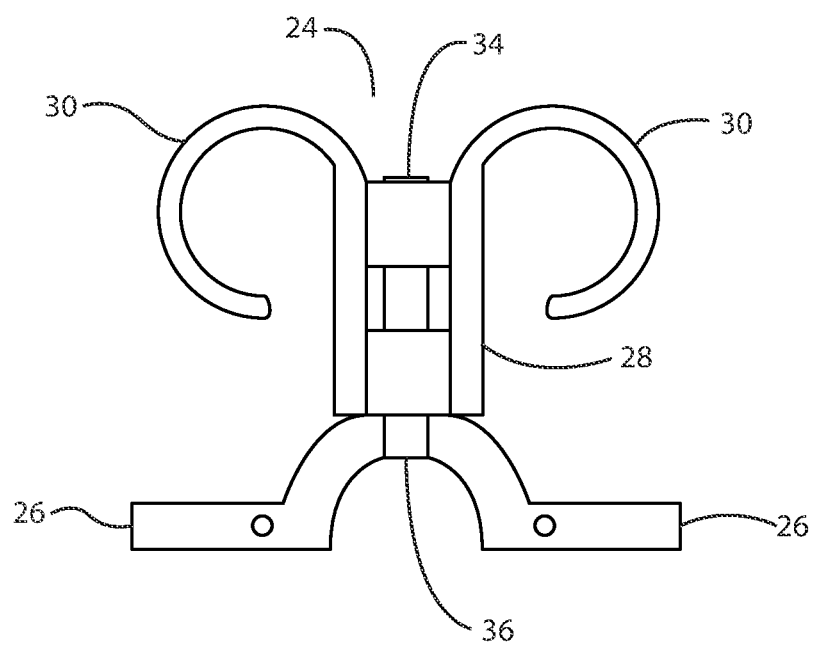
FIG. 8 is a front view a perspective view a rack hanger of the present invention.

With reference to FIGS. 1 and 8, the first embodiment 10A of the urine collection bag assembly of the present invention includes an inlet adapter 24. The inlet adapter 24 has an inlet 34 and an outlet 36 and includes legs 26, a valve body portion 28 and curved rack hooks 30. The legs 26 allow the inlet adapter 24 to be attached to a side of an upper end 32 the urine collection bag 12. The valve body portion 28 is adapted to receive the one-way flow control valve 18. The curved rack hooks 30 extend from the valve body portion 28 and allow the urine collection bag assembly to be hung from a rack (not shown) which is the standard practice in most hospitals. The inlet 34 of the inlet adapter 24 is configured to connect to a catheter connection tube 38 (see FIG. 1) which interconnects the urine collection bag assembly with a urinary catheter (not shown). The outlet 36 of the inlet adapter 24 interconnects via tubing with the inlet 14 of the urine collection bag 12.

With reference to FIGS. 4-7, the sampling valve 20 has a hollow cylindrical valve inlet portion 40 and a hollow cylindrical valve outlet portion 42. The hollow cylindrical inlet and outlet portions 40 and 42 being in fluid communication. Disposed between the sampling valve hollow cylindrical inlet portion 40 and the sampling valve hollow cylindrical outlet portion 42 is a hollow cylindrical slide passageway 44. Disposed within the hollow cylindrical slide passageway 44 is a valve slider 46. The valve slider 46 has right and left cylindrical end portions 60 and 61 which have an outside diameter 48 which is configured to be a tight slip fit or friction fit with an inside diameter 62 of the hollow cylindrical slide passageway 44. The fit between the inside diameter 62 of the hollow cylindrical slide passageway 44 and outside diameter 48 of the right and left cylindrical end portions 60 and 61 of the valve slider 46 should be watertight. When either of the right or left cylindrical end portions 60 and 61 are disposed between the hollow cylindrical inlet and outlet portions 40 and 42, fluid communication between the hollow cylindrical inlet and outlet portions 40 and 42 is cutoff.

Disposed between the right and left cylindrical end portions 60 and 61 of the valve slider 46 is a cylindrical intermediate portion 50. The cylindrical intermediate portion 50 has an outside diameter 64 substantially smaller than that of the hollow, cylindrical slide passageway 44 such that urine will freely flow through the hollow cylindrical valve inlet and outlet portions 40 and 42, when the cylindrical intermediate portion 50 of the valve slider 46 is moved to a position between the hollow cylindrical valve inlet and outlet portions 40 and 42.

Secured to the right end portion 61 of the valve slider 46 is a right end cap 52 and secured to the left cylindrical end portion 60 of the valve slider 46 is a left end cap 54. The right and left end caps 52 and 54 are configured to have an inside diameter 66 which allows the right and left end caps 52 and 54 to freely slide over an outside diameter 68 of the slide passageway 44. The dimensions of the right and left cylindrical end portions 60 and 61 and right and left end caps 52 and 54 are configured such that when the left end cap 54 is pushed fully to the right, the sampling valve 20 is in a closed position. (See FIG. 5.) Similarly, when the right end cap 52 is pushed fully to the left, the sampling valve 20 is in an open position. (See FIG. 6.)

The right and left end caps 52 and 54 may be attached to the right and left end portions by a number of means. For example, in FIG. 4, the left end cap 54 is press fit and then glued to the end portion 61, whereas the right end cap 52 is pinned and glued to the right end portion 61 via a pin 56.

Disposed at a lower end 70 of the hollow cylindrical valve outlet portion 42 are screw threads 72. The screw threads 72 allow for the ready attachment of accessories with mating threads 80 such as urine sampling bottles (not shown) or a screw cap 74 (see FIG. 7) when the sampling valve 20 is not in use. The screw cap 74 is equipped with a cylindrical inset 76 that engages and seals the lower end 70 of hollow cylindrical valve outlet portion 42. The lower end 70 of hollow cylindrical valve outlet portion 42 is also equipped with a ledge 78 which acts as positive stop for the screw cap 74.

The urine collection bag 12 will typically be made by heat sealing or otherwise securing flexible, precut flat sheets of a biologically inert plastic material to form a bag having an internal volume. Suitable materials for the urine collection bag 12 include polyvinyl chloride, polyethylene and polypropylene. Other materials may also be suitable. The urine collection bag 12 would also typically be printed with fully graduated volume measurements 82 (see FIG. 1). Typical dimensions for the urine collection bag 12 are a width approximately 22 centimeters and a height of approximately 30 centimeters. The urine collection bag 12 will typically have a volume of about 3000 milliliters.

Similarly, the one-way flow control valve 18 and sampling valve 20 will typically be made of an injection moldable biologically inert plastic material. Polyethylene and polypropylene are two such suitable materials, which are known in the art. Other plastic materials, such as polyvinyl chloride are also suitable.

The one-way flow control valve 18 of the urine collection bag 12 and a catheter connection tube 38 interconnecting the urine collection bag assembly and a urinary catheter (not shown) may be equipped with antibacterial coatings to further minimize the likelihood that any urine drips that may reside in the catheter connection tube 38 or the one-way flow control valve 18 would cause a urinary tract infection.

Figure 9:
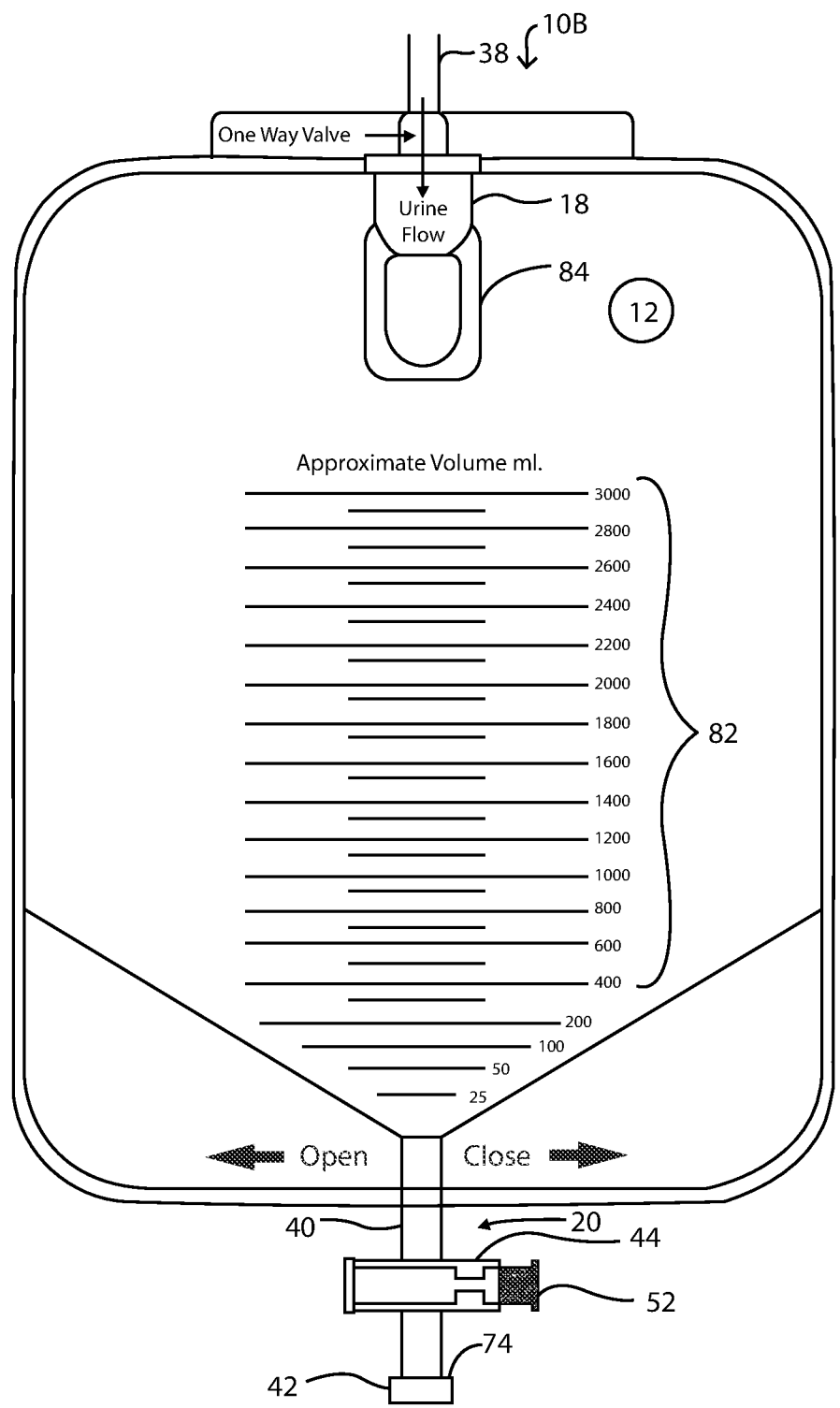
FIG. 9 is a schematic front plan view of a second embodiment of the urine collection bag of the present invention.
Figure 10:
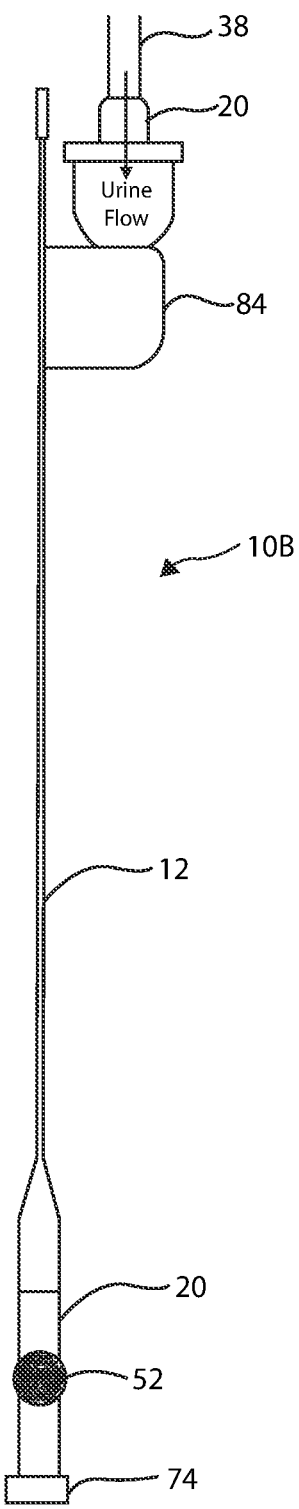
FIG. 10 is a schematic side view of the alternative embodiment of the urine collection bag of FIG. 1.

With reference to FIGS. 9-10, a second embodiment 10B of the urine collection bag assembly of the present invention is shown. Like the first embodiment 10A, the second embodiment 10B includes a urine collection bag 12, a one-way flow control valve 18 disposed near the top of the urine collection bag 12 and a sampling valve 20 disposed at a bottom of the urine collection bag 12. In the second embodiment 10B, the one-way flow control valve 18 includes an integral urine drip container 84 and the integral flow control valve and drip container are mounted to a side of the urine collection bag 12, rather than exterior to the bag. Otherwise, the construction details are the same as for the first embodiment 10A.

Figure 11:
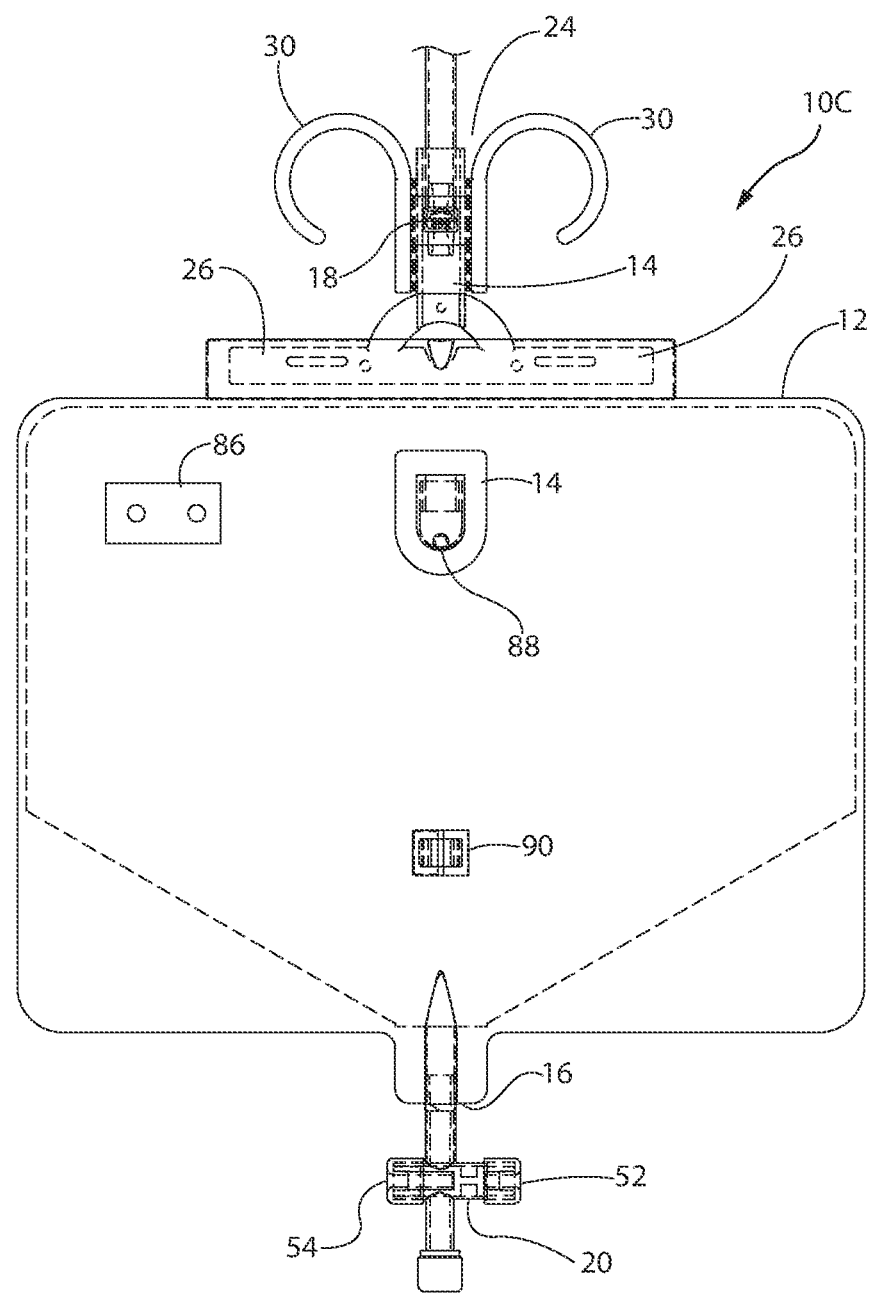
FIG. 11 is a schematic front plan view of a third exemplary embodiment of the urine collection bag of the present invention.
Figure 12:
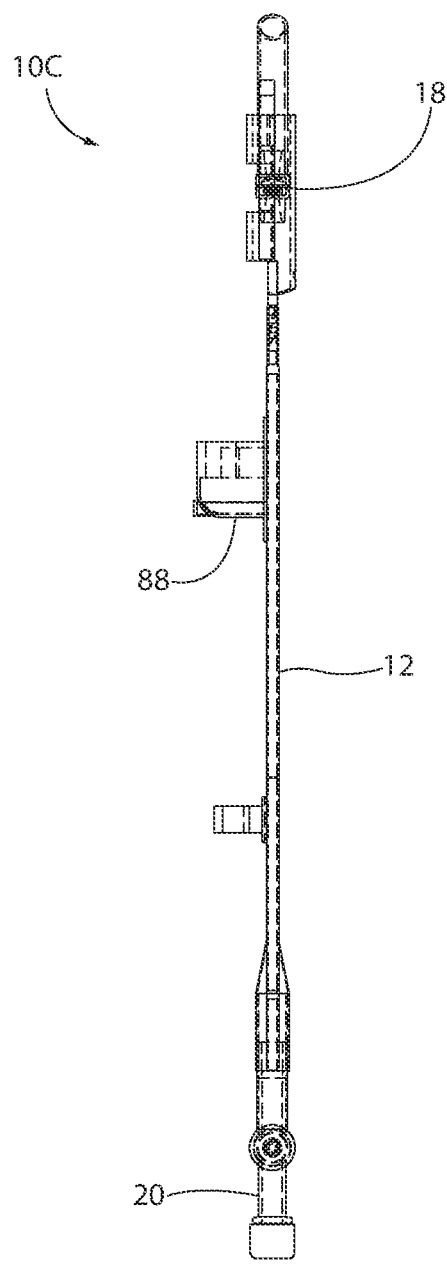
FIG. 12 is a schematic side view of the urine collection bag of FIG. 11.
Figure 13:
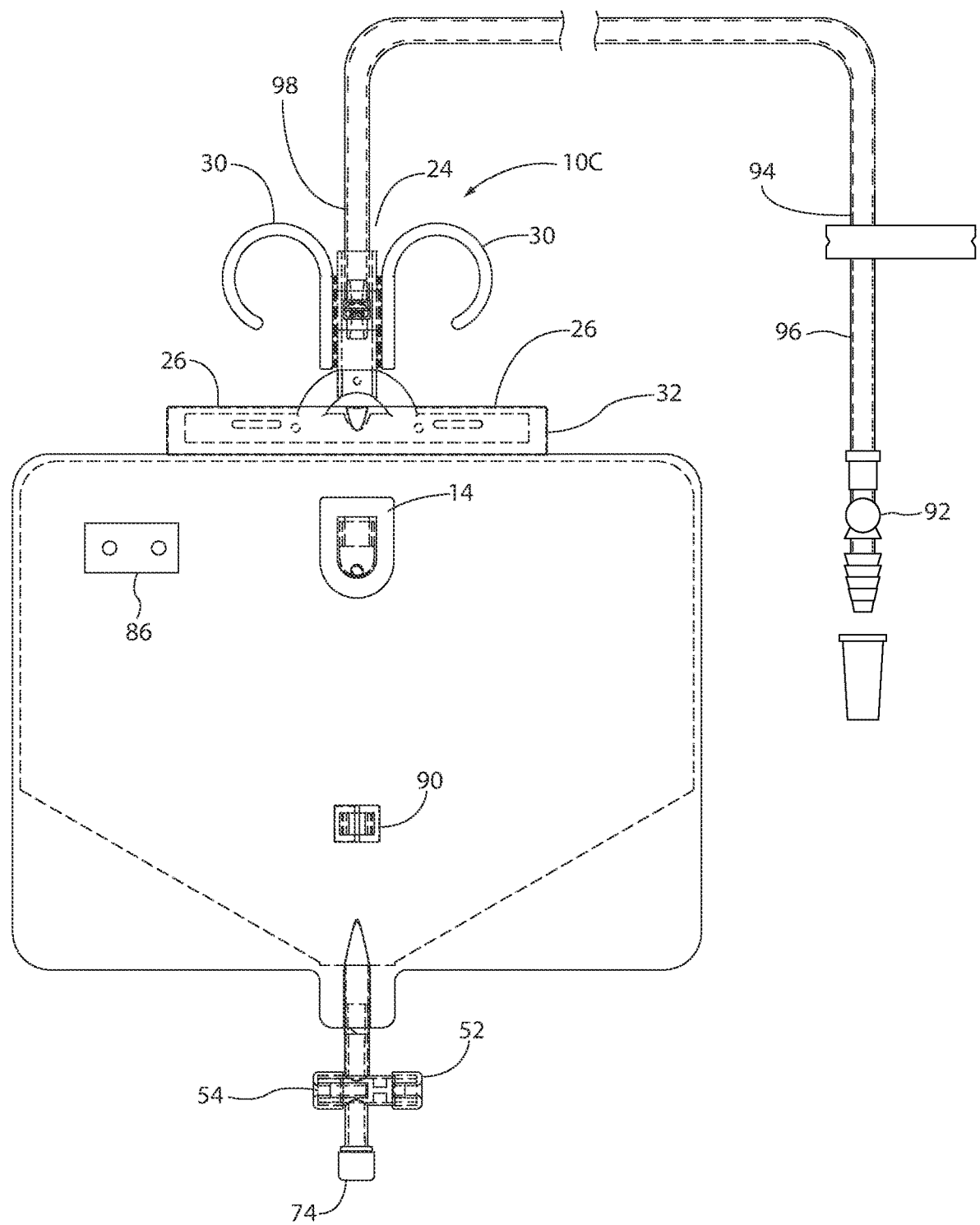
FIG. 13 is a schematic rear plan view of the urine collection bag of FIG. 11.

With reference to FIGS. 11-13, a third embodiment 10C of the urine collection bag assembly of the present invention is shown. Similar to the first and second embodiments 10A and 10B, the third embodiment 10C includes the urine collection bag 12, the one-way flow control valve 18 disposed above the inlet 14 of the urine collection bag 12 and the sampling valve 20 located below the outlet 16 of the urine collection bag 12. The one-way flow control valve 18, urine collection bag 12 and the sampling valve 20 are in fluid communication.

With reference to FIGS. 11-13 and FIG. 8, the third embodiment 10C of the urine collection bag assembly also includes the inlet adapter 24 which includes legs 26, which allow the inlet adapter 24 to be attached to an upper end 32 the of urine collection bag, the valve body portion 28 which is configured to retain the one-way flow control valve 18 and the curved rack hooks 30, allow the third embodiment 10C of the urine collection bag assembly 10 to be hung from a rack.

With continued reference to FIGS. 11-13, in addition to the features of the first and second embodiments 10A and 10B of the urine collection bag assembly, the third embodiment 10C also features a bacterial monitoring wick 88, an air vent 86, a sampling valve clip 90, a sampling port 92 and sterilized sampling valve caps, i.e. end right and left end caps 52 and 54 and screw cap 74.

The bacterial monitoring wick 88 of the urine collection bag assembly 10C is disposed in the inlet 14 of the urine collection bag 12. Being disposed in the inlet 14, the bacterial monitoring wick 88 is in direct contact with urine drainage flow. If a patient's urine becomes contaminated, suggesting an infection, the bacterial monitoring wick 88 will change color, thereby promoting replacement of the urine collection bag assembly and of the catheter which directs urine into the collection bag.

The air vent 86 of the urine collection bag assembly 10C is typically disposed on one or both sides the urine collection bag 12. The air vent 86 is a pressure release valve which is configured to release air upon air accumulating the in the urine collection bag 12 and exceeding a predetermined pressure.

The third embodiment 10C of the urine collection bag assembly also includes a length of flexible tubing 94 having a distal end 98 which connects to the inlet adapter 24 and a proximal end 96 which connects to a sampling port 92. The sampling port 92 may be a needle sampling port or a needle free sampling port. In use, the proximal end 96 of the flexible tubing 94 is connected to another length of tubing that connects to a catheter (not shown). The sampling port 92 allows urine samples to be drawn with a syringe.

The sampling valve clip 90 of the third embodiment 10C of the urine collection bag assembly is disposed on the urine collection bag 12. The sampling valve clip 90 is configured so that the sampling valve 20 is removably attachable to the clip. The sampling valve clip 90 allows the sampling valve 20 to be clipped up to the bag and dropped back into position as may be desired during for convenience or protection and safety.

The third embodiment 10C of the urine collection bag assembly also includes replaceable, sterile right and left end caps 52 and 54 and sterile screw caps 74 for the sampling valve 20.

The one-way flow control valve 18 of the third embodiment 10C of the urine collection valve assembly may be a duckbill style valve. Duckbill style valves are known in the art and are commercially available. One suitable source for duckbill valves is Minivalve, Inc. which has a U.S. Office located at 6100 Oak Street Blvd., Suite 200, Cleveland, Ohio 44131. Sampling ports 92 are also known in the art and commercially available. One suitable source for sampling ports is Carmo A/S, Hoejvangen 19, 3060 Espergaerde, Denmark. Bacterial monitoring wicks 88 are known in the art and are commercially available from Siemens Manufacturing Co. Inc. located at 410 W. Washington St., Freeburg, IL 62243.

The foregoing detailed description and appended drawings are intended as a description of the presently preferred embodiment of the invention and are not intended to represent the only forms in which the present invention may be constructed and/or utilized. Those skilled in the art will understand that modifications and alternative embodiments of the present invention which do not depart from the spirit and scope of the foregoing specification and drawings, and of the claims appended below are possible and practical. It is intended that the claims cover all such modifications and alternative embodiments.

What is claimed is:

1. A urine collection bag assembly comprising:
    a urine collection bag having an inlet and an outlet;
    a one-way flow control valve having an inlet and an outlet, the outlet of the one-way flow control valve connected to the inlet of the urine collection bag; the inlet of the one-way flow control valve being attachable to a urinary catheter, wherein the one-way flow control valve prevents the backflow of urine out of the urine collection bag;
    a sampling valve disposed below and exterior to the inlet of the urine collection bag, the sampling valve having an inlet and an outlet, the inlet of the sampling valve connected to the outlet of the urine collection bag;
        a bacterial monitoring wick, which changes color in response to detecting a a bacterial infection in urine, the bacterial monitoring wick disposed within the inlet of the urine collection bag;
        an air vent for releasing air trapped within the urine collection bag, the air vent attached to a side of the urine collection bag;
        a sampling port for the sampling of urine, the sampling port connected to the inlet of the urine collection bag;
        a sampling valve clip, to which the sampling valve is removably attachable; and
    curved hooks extending upwardly from a top of the urine collection bag wherein the curved hooks allow the urine collection bag to be hung from a rack.

2. A urine collection bag assembly comprising:
    a urine collection bag having an inlet and an outlet;
    a one-way flow control valve having an inlet and an outlet, the outlet of the one-way flow control valve connected to the inlet of the urine collection bag; the inlet of the one-way flow control valve being attachable to a urinary catheter, wherein the one-way flow control valve prevents the backflow of urine out of the urine collection bag;
    a sampling valve having an inlet and an outlet, the inlet of the sampling valve connected to the outlet of the urine collection bag;
    a bacterial monitoring wick, which changes color in response to detecting a a bacterial infection in urine, the bacterial monitoring wick disposed within the inlet of the urine collection bag; and
    an air vent, which releases air trapped within the urine collection bag, the air vent attached to a side of the urine collection bag.

3. The urine collection bag assembly of claim 2, further including a sampling port for the sampling of urine, the sampling port connected to the inlet of the urine collection bag.

4. The urine collection bag assembly of claim 2, further including a sampling valve clip, to which the sampling valve is removably attachable.

5. The urine collection bag assembly of claim 2, wherein the one-way flow control valve is a duckbill style valve.

6. The urine collection bag assembly of claim 2, wherein the collection bag includes a graduated volume scale.

7. The urine collection bag assembly of claim 2, wherein the sampling valve includes a horizontal slider to which are attached replaceable, sterile caps.

8. The urine collection bag assembly of claim 2, wherein the urine collection bag, one-way flow control valve and sampling valve are made from biologically inert materials.

9. The urine collection bag assembly of claim 7, wherein the urine collection bag, one-way flow control valve, and sampling valve each comprise one or more materials selected from the group consisting of polypropylene, polyethylene and poly vinyl chloride.

10. A urine collection bag assembly comprising:
    a urine collection bag having an inlet and an outlet;
    a one-way flow control valve having an inlet and an outlet, the outlet of the one-way flow control valve connected to the inlet of the urine collection bag; the inlet of the one-way flow control valve being attachable to a urinary catheter, wherein the one-way flow control valve prevents the backflow of urine out of the urine collection bag;
    a sampling valve having an inlet and an outlet, the inlet of the sampling valve connected to the outlet of the urine collection bag; and
    a bacterial monitoring wick, which changes color in response to detecting a bacterial infection in urine, the bacterial monitoring wick disposed within the inlet of the urine collection bag.

11. The urine collection bag assembly of claim 10, further including a sampling port for the sampling of urine, the sampling port connected to the inlet of the urine collection bag.

12. The urine collection bag assembly of claim 10, further including an air vent attached to a side of the urine collection bag, the air vent functioning to release air trapped within the urine collection bag.

13. The urine collection bag assembly of claim 10, further including a sampling valve clip, to which the sampling valve is removably attachable.

14. The urine collection bag assembly of claim 10, wherein the one-way flow control valve is a duckbill style valve.

15. The urine collection bag assembly of claim 10, wherein the sampling valve includes a horizontal slider to which are attached replaceable end caps.

16. The urine collection bag assembly of claim 15, wherein the end caps are sterile.

17. The urine collection bag assembly of claim 10, wherein the outlet of the sampling valve is threaded to engage a screw cap, the screw cap having a raised inset which seals the outlet of the sampling valve when engaged.

18. The urine collection bag assembly of claim 16, wherein the screw cap is sterile.

19. The urine collection bag assembly of claim 10, wherein the one-way flow control valve is disposed on the side of the urine collection bag.

20. The urine collection bag assembly of claim 10, wherein the collection bag includes a graduated volume scale.

* * * * *